(12) United States Patent
Ambati

(10) Patent No.: US 8,481,508 B2
(45) Date of Patent: Jul. 9, 2013

(54) ULTRA-SMALL RNAS AS TOLL-LIKE RECEPTOR-3 ANTAGONISTS

(75) Inventor: Jayakrishna Ambati, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 12/918,548

(22) PCT Filed: Feb. 20, 2009

(86) PCT No.: PCT/US2009/001106
§ 371 (c)(1), (2), (4) Date: Jan. 11, 2011

(87) PCT Pub. No.: WO2009/105260
PCT Pub. Date: Aug. 27, 2009

(65) Prior Publication Data
US 2011/0097390 A1   Apr. 28, 2011

Related U.S. Application Data

(60) Provisional application No. 61/030,487, filed on Feb. 21, 2008.

(51) Int. Cl.
*C12N 15/11* (2006.01)
*A61K 48/00* (2006.01)
*C07H 21/02* (2006.01)
*C07H 21/04* (2006.01)

(52) U.S. Cl.
USPC .................................. 514/44 A; 536/24.5

(58) Field of Classification Search
USPC .................. 514/44; 536/24.1, 24.5
See application file for complete search history.

(56) References Cited

U.S. PATENT DOCUMENTS

| 5,632,984 A | 5/1997 | Wong et al. |
| 2005/0282188 A1* | 12/2005 | Haeberli et al. ............... 435/6 |
| 2006/0147456 A1 | 7/2006 | Lebecque et al. |

(Continued)

FOREIGN PATENT DOCUMENTS

| EP | 1 224 9399 A1 | 7/2002 |
| WO | WO 2006/014653 | 2/2006 |

OTHER PUBLICATIONS

Kleinman et al. (Molecular Therapy, published online Oct. 11, 2011, vol. 20, No. 1:101-108).*
Kleinman et al. (Nature, 2008 Col. 452:591-598).*

(Continued)

*Primary Examiner* — Terra Cotta Gibbs
(74) *Attorney, Agent, or Firm* — Crowell & Moring LLP

(57) ABSTRACT

Provided are methods and compositions for the treatment or prevention of macular degeneration or other diseases or disorders associated with activation of TLR3. Administration of double stranded RNAs having a length of 22 nucleotides or less treats or prevents macular degeneration or other diseases or disorders associated with activation of TLR3 due to the ability of the RNAs to bind to but not activate TLR3. Furthermore, all double stranded RNAs (both targeted and non-targeted) of 22 nucleotides or less in length can bind to but not activate TLR3 and thereby treat or prevent such conditions. Also provided of a method for increasing the specificity of a desire siRNA target knockdown, the method comprising administering an amount of a target siRNA sufficient to knockdown a target gene and an amount of a double stranded RNA of 22 nucleotides or less which prevents the target siRNA from activating TLR3.

18 Claims, 16 Drawing Sheets

U.S. PATENT DOCUMENTS

2006/0211752 A1 9/2006 Kohn et al.
2007/0232622 A1* 10/2007 Lipford et al. ............. 514/258.1
2007/0238654 A1* 10/2007 Deschatelets et al. ............. 514/9
2007/0281328 A1 12/2007 Hsu et al.

OTHER PUBLICATIONS

Dong-Ho Kim et al., Synthetic dsRNA Dicer substrates enhance RNAI potency and efficacy, Nature Technology, vol. 23, No. 2, Feb. 2005, pp. 222-226.

Walt F. Lima et al., Human Dicer Binds Short Single-strand and Double-strand RNA with High Affinity and Interacts with Different Regions of the Nucleic Acids, Journal of Biological Chemistry, Jan. 23, 2009, vol. 284, No. 4, pp. 2535-2548.

M.V. Kumar et a., Double Stranded RNA (poly I:C) Up Regulates Toll-Like Receptor 3 and Induces Interferon β (IFN—β) in Human Retinal Pigment Epithelial Cells, Investigative Ophthalmology & Visual Science 2003, 44: E-Abstract 738.

J.O. Oh et al., Protective Effect of a Synthetic Polynucleotide Complex (Poly I:C) on Ocular Lesions Produced by Trachoma Agent in Rabbits, Infection and Immunity, Jun. 1970, pp. 566-573, vol. 1, No. 6.

Jorma Tissari et al., INF-alpha Enhances TLR3-Mediated Antiviral Cytokine Expression in Human Endothelial and Epithelial Cells by Up-Regulating TLR3 Expression, The Journal of Immunology, 2005, pp. 4289-4294.

Matam Vijay Kumar et al., Innate immunity in the retina: Toll-like receptor (TLR) signaling in human retinal pigment epithelial cells, Journal of Neuroimmunology 153 (2004), pp. 7-15.

Supplemental Partial European Search Report dated Dec. 5, 2011.

U.S. Appl. No. 11/219,582, Jun. 8, 2006, Quay

Kim, Sirmune Activation by siRNA/Liposome, Oct. 31, 2007.

Receptor 3 and Geographic Atrophy, Oct. 2, 2008 in Age-Related Macular.

International Search Report dated Jul. 6, 2009 (One (1) page).

* cited by examiner

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
uaaggcuaug aagagauact t                                                  21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uaaggcuaug aagagauatt                                                    20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
uaaggcuaug aagagautt                                                     19

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
uaaggcuaug aagatt                                                        16

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
-continued

<400> SEQUENCE: 5
uaaggcuaug att                                                            13

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
uaaggcuaug aagatt                                                         16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
ucuucauagc cuuatt                                                         16
```

US 8,481,508 B2

ULTRA-SMALL RNAS AS TOLL-LIKE RECEPTOR-3 ANTAGONISTS

This application is a national stage of PCT International Application No. PCT/US2009/001106, filed Feb. 20, 2009, which claims priority under 35 U.S.C. §119 to U.S. Provisional Application No. 61/030,487, filed Feb. 21, 2008, the entire disclosure of which is herein expressly incorporated by reference.

The instant application contains a Sequence Listing which has been submitted via EFS-web and is hereby incorporated by reference in its entirety.

FIELD OF THE INVENTION

The present invention relates to the ability of ultra-small RNAs to act as toll-like receptor-3 (TLR3) antagonists.

BACKGROUND

The macula is the part of the retina which is responsible for central vision. Age-related macular degeneration is a chronic eye disease that occurs when tissue in the macula deteriorates. Macular degeneration affects central vision, but not peripheral vision. Macular degeneration is the leading cause of severe vision loss in people age 60 and older.

There are two forms of age-related macular degeneration: dry and wet. Dry macular degeneration is the most common type of macular degeneration and occurs when cells of the macula slowly begin to break down. Yellow deposits called "drusen" form under the retina between the retinal pigmented epithelium (RPE) and Bruch's membrane, which supports the retina. The drusen deposits are debris associated with compromised cell metabolism in the RPE. Eventually there is a deterioration of the macular regions associated with the drusen deposits resulting in a loss of central vision.

Wet macular degeneration occurs when abnormal blood vessels grow behind the macula. These vessels are fragile and can leak fluid and blood, which result in scarring of the macula and raise the potential for rapid, severe damage. Bruch's membrane breaks down, usually near drusen deposits. This is where new blood vessel growth, or neovascularization, occurs. Central vision can become distorted or lost entirely in a short period of time, sometimes within days. Wet macular degeneration is responsible for about 10 percent of the cases of age-related macular degeneration, but it accounts for about 90 percent of the cases of legal blindness.

SUMMARY OF THE INVENTION

In one aspect the present invention relates to a method of treating or preventing macular degeneration. The method comprises exposing a retinal or choroidal cell to a toll-like receptor 3 (TLR3)-antagonistic effective amount of a double-stranded RNA of 22 nucleotides or shorter length which binds to but does not activate the activity of a TLR3.

In yet another aspect, the present invention relates to a method of treating or preventing a disease or disorder associated with activation of TLR3. The method comprises exposing a subject in need thereof to a toll-like receptor 3 (TLR3)-antagonistic effective amount of a double-stranded RNA of 22 nucleotides or shorter length which binds to but does not activate the activity of a TLR3

In another aspect, the present invention relates to a composition for the treatment or prevention of macular degeneration. The composition comprises a sequence-nonspecific or sequence-specific double-stranded RNA of 22 nucleotides or shorter length which binds to but does not activate the activity of a TLR3.

In yet another aspect, the present invention relates to a method for increasing the specificity of a desired siRNA target knockdown. The method comprises administering an amount of a target siRNA sufficient to knockdown a target gene and an amount of a double stranded RNA of 22 nucleotides or less which prevents the target siRNA from activating TLR3.

In still another aspect the present invention relates to a method for screening for a compound that antagonizes TLR3. The method comprises contacting TLR3 or binding fragment thereof with a test compound, and determining if a complex is formed between TLR3 or binding fragment thereof and the test compound.

Other systems, methods, features and advantages of the present invention will be or become apparent to one with skill in the art upon examination of the following drawings and detailed description. It is intended that all such additional systems, methods, features and advantages be included within this description, be within the scope of the present invention, and be protected by the accompanying claims.

μg) does not block the effects of Ampligen® (right panel). The photographs were taken 10 days after Ampligen® and antibody injection.

Figure 11:
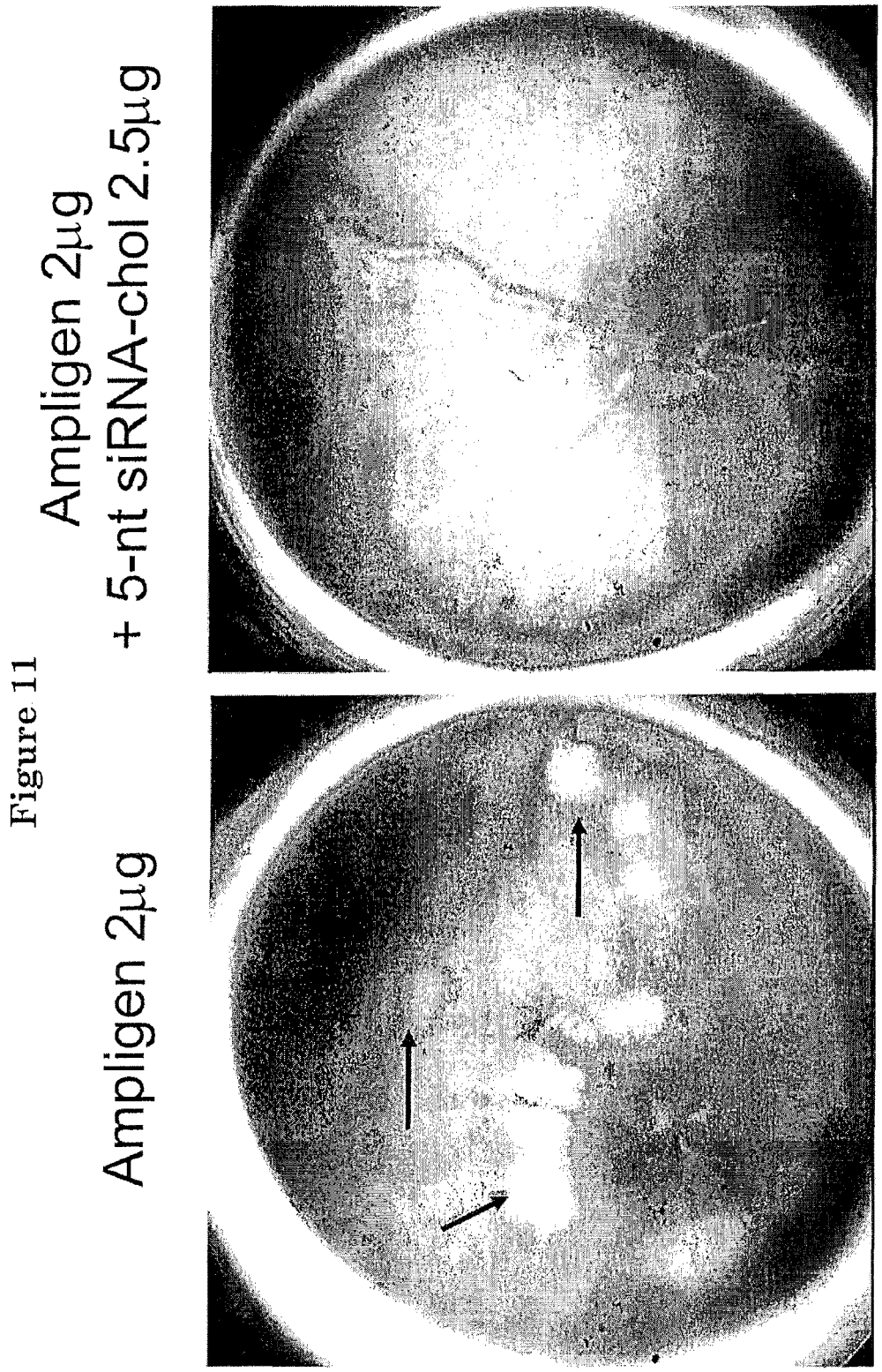

FIG. 11 provides color fundus photographs showing that retinal degeneration induced by intravitreous administration of Ampligen® (poly I:C12U; 2 μg) in wild-type mice (left panel) does not occur when blunt end double stranded 5-nt-dsRNA conjugated to cholesterol (chol) is co-administered (right panel). The photographs were taken 10 days after Ampligen® and 5-nt-dsRNA injection.

Figure 12:
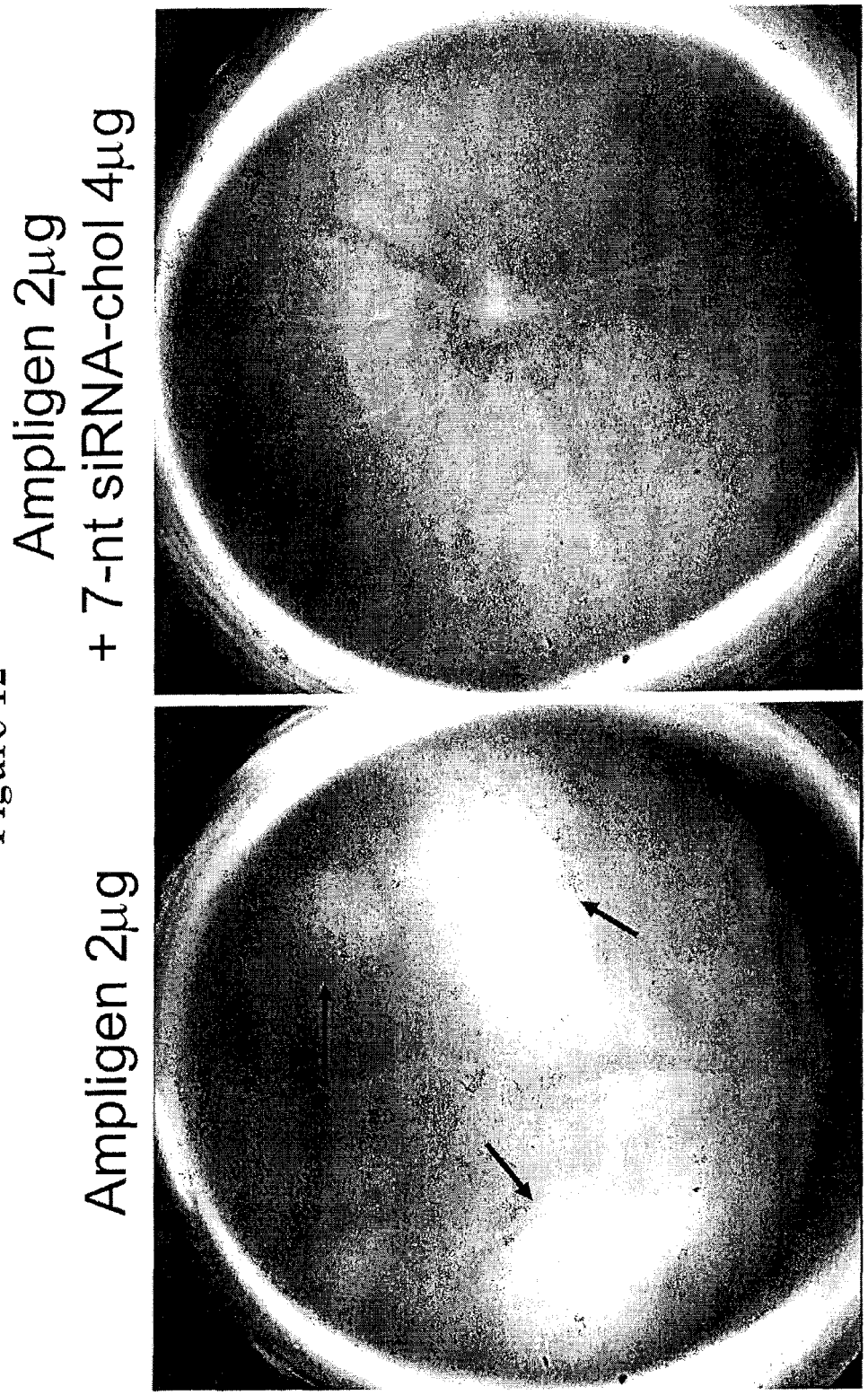

FIG. 12 provides color fundus photographs showing that retinal degeneration induced by intravitreous administration of Ampligen® (poly I:C12U; 2 μg) in wild-type mice (left panel) does not occur when blunt end double stranded 7-nt-dsRNA (4 μg) conjugated to cholesterol (chol) is co-administered (right panel). The photographs were taken 10 days after Ampligen® and 7-nt-dsRNA injection.

Figure 13:
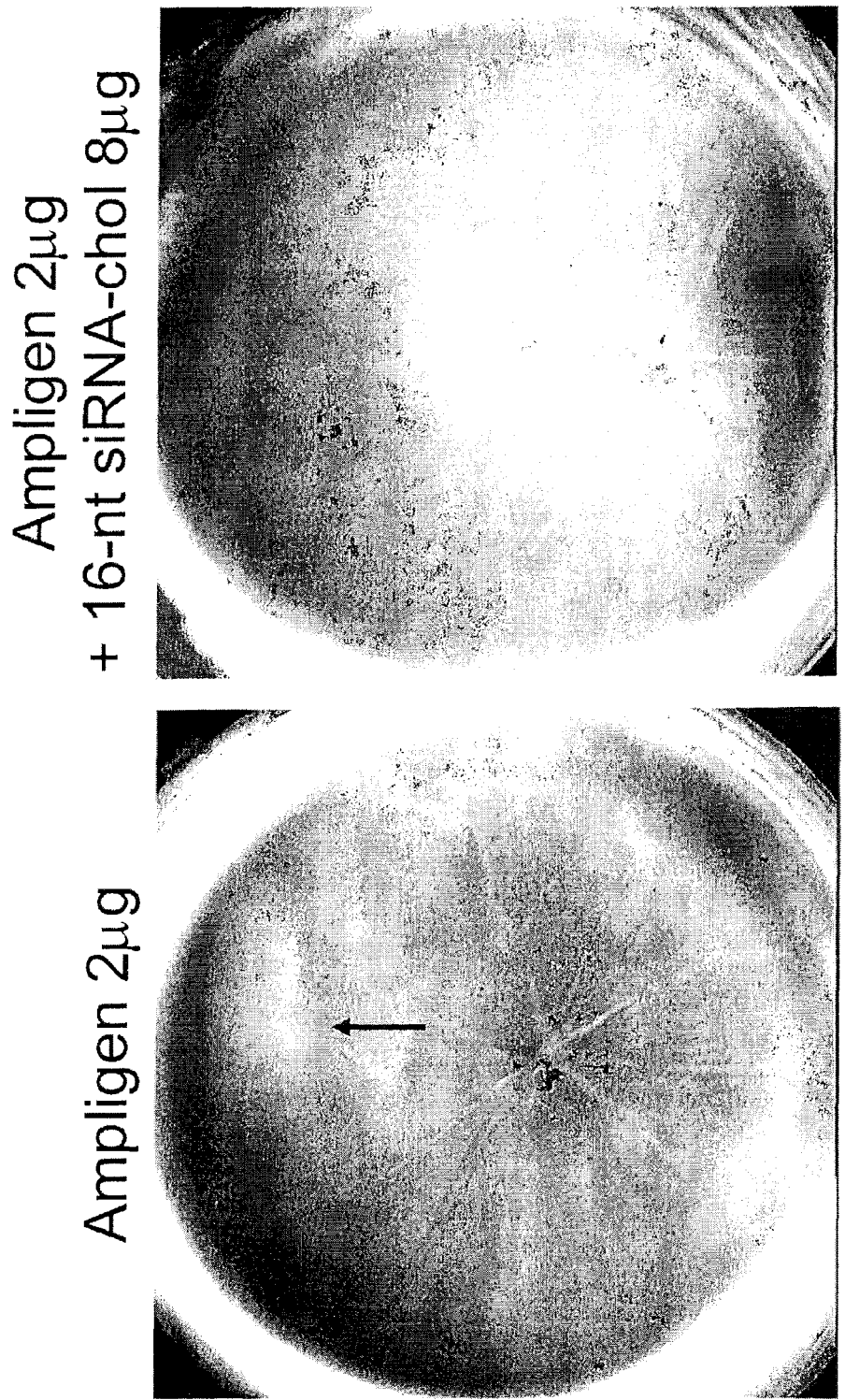

FIG. 13 provides color fundus photographs showing that retinal degeneration induced by intravitreous administration of Ampligen® (poly I:C12U; 2 μg) in wild-type mice (left panel) does not occur when cholesterol (chol)-conjugated double stranded 16-nt-dsRNA (8 μg), which contains 14 base pairs on each strand with 2-nt overhangs on each strand, is co-administered (right panel). The photographs were taken 10 days after Ampligen® and 16-nt-dsRNA injection.

Figure 14:
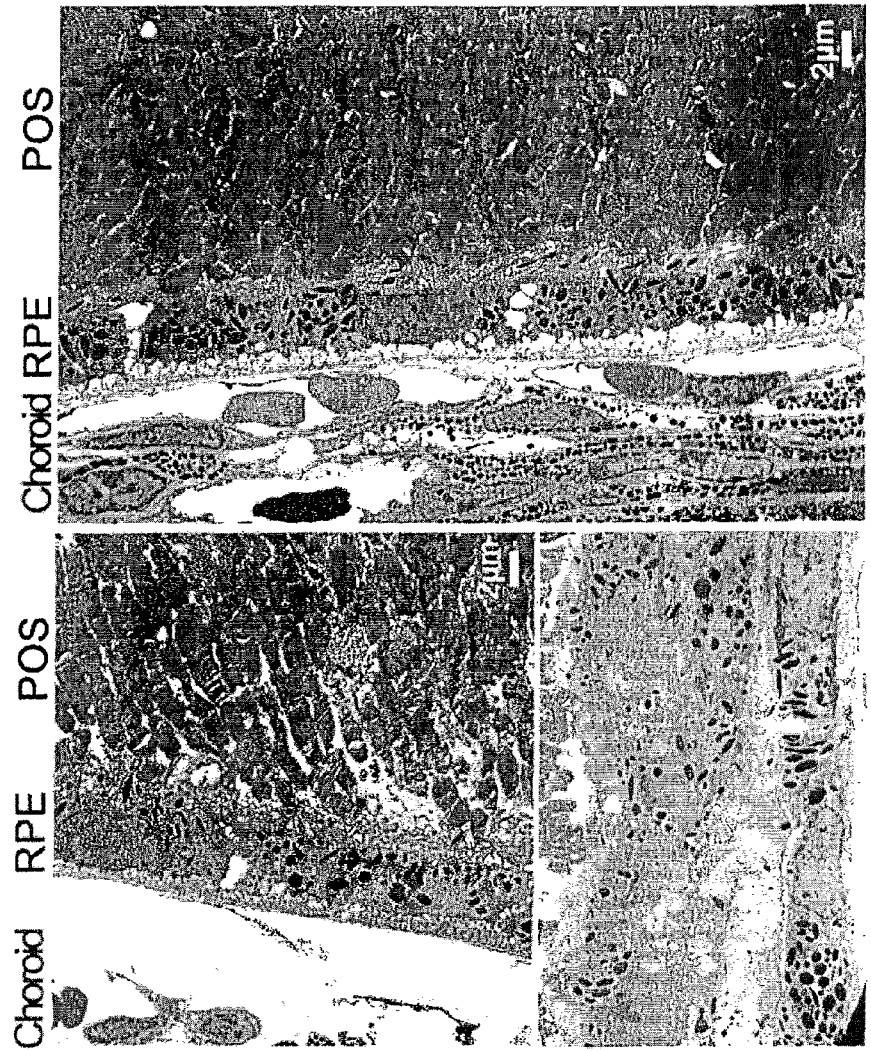

FIG. 14 provides transmission electron micrographs showing that intravitreous administration of Ampligen® (poly I:C12U; 2 μg) in wild-type mice (left panels) results in photoreceptor outer segment (POS) damage (red arrowheads; top left) and degeneration of retinal pigmented epithelial (RPE) cells in wild-type mice. Co-administration of 16-nt-dsRNA-chol (8 μg) preserves the anatomical architecture of the POS and RPE. The images were taken 2 weeks after drug administration.

Figure 15:
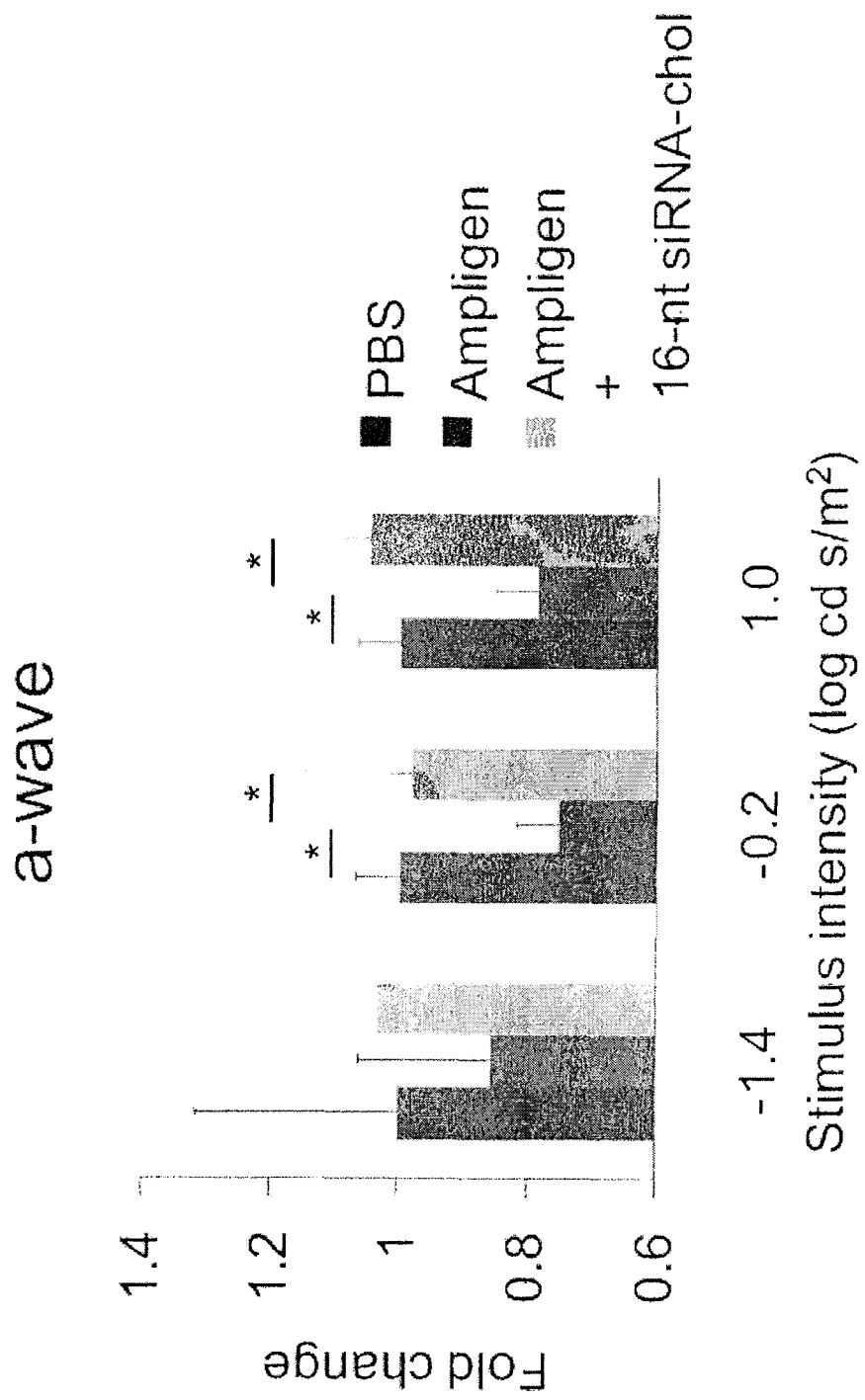

FIG. 15 provides scotopic electroretinograms (ERG) showing that a-wave amplitude is attenuated by intravitreous administration of Ampligen® (poly I:C12U; 2 μg) in wild-type mice, as compared to phosphate buffered saline (PBS). Co-administration of 16 nt-dsRNA-chol (8 μg) rescued the ERG a-wave attenuation.

Figure 16:
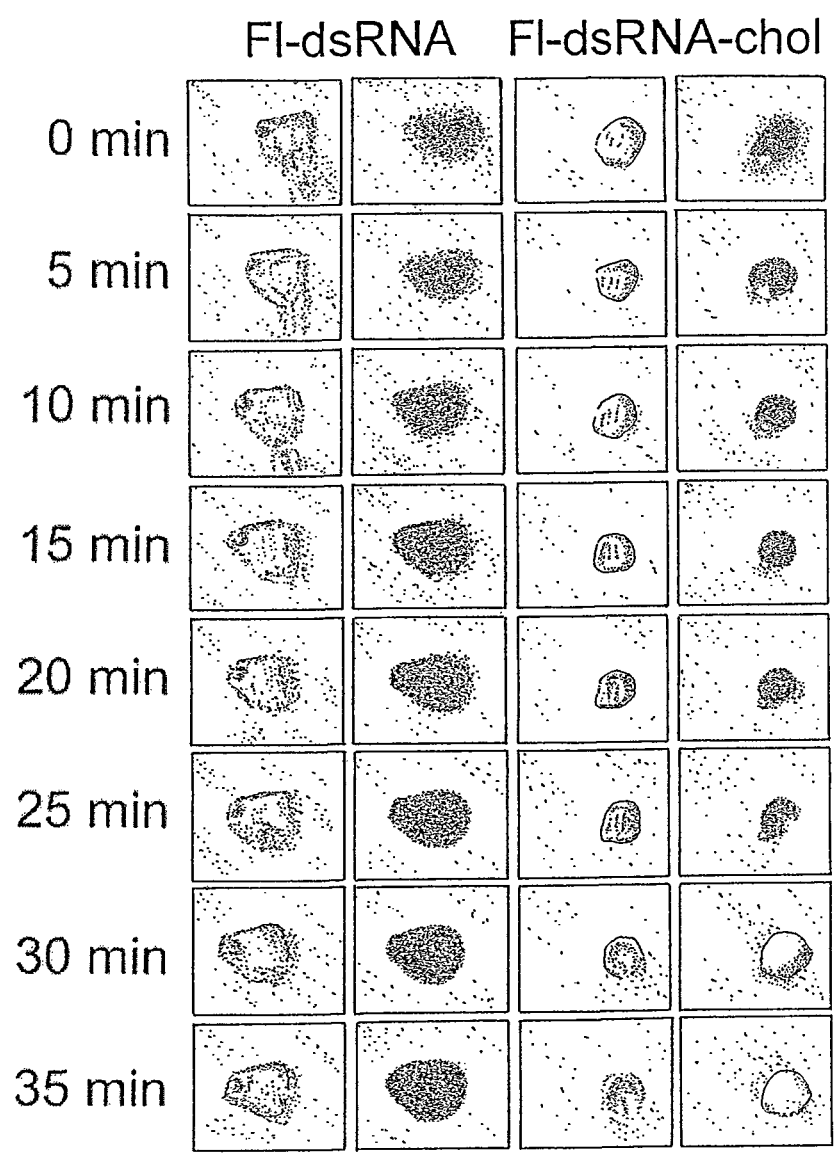

FIG. 16 shows that double stranded RNA requires a cell permeating entity for internalization by mammalian cells. Mouse endothelial cell cultures were exposed to fluorescein-conjugated dsRNA (Fl-dsRNA) followed by time-lapse confocal microscopy (left panel, Nomarski, right panel, green channel). When Fl-dsRNA was conjugated with cholesterol (Fl-dsRNA Chol), a cell-permeant entity, there was robust LEC internalization.

DETAILED DESCRIPTION

Toll-like receptors (TLRs) are type I transmembrane proteins involved in innate immunity by recognizing microbial conserved structures. Toll-like receptors can help activate the adaptive immune response, thereby linking innate and acquired immune responses. Ten TLRs (named TLR1 to TLR10) have been identified in humans, with each TLR being specific for a different microbial-associated molecular pattern. The present inventor has surprisingly found that double-stranded RNAs of 22 nucleotides (nt) or shorter length bind to but do not activate toll-like receptor-3 (TLR3) and, among other things, can inhibit the geographic atrophy of macular degeneration.

In one aspect, methods and compositions are provided for the treatment or prevention of macular degeneration, including geographic atrophy of macular degeneration such as the geographic atrophy of dry macular degeneration. For example, administration of antagonists of TLR3 inhibits the geographic atrophy of macular degeneration such as the geographic atrophy of dry macular degeneration. Geographic atrophy includes choroidal atrophy and retinal atrophy. Compositions and methods for blocking the activity of TLR3 for the treatment and/or prevention of macular degeneration are provided.

Any double-stranded RNA of 22 nucleotides or shorter length which binds to but does not activate TLR3 may be used in the present invention. Natural agonists for TLR3 include viral double-stranded RNA. Any natural agonist of TLR3 can be converted to an antagonist by shortening the length to 22 nucleotides or less. Such shortened double-stranded RNAs bind to but do not activate TLR3 activity. Preferably, the length of the double-stranded RNA is 5-22 nucleotides. Preferably, the length of the double-stranded RNA is 5-15 nucleotides. More preferably, the length is 7-11 nucleotides.

In addition, other ligands can also be used to antagonize TLR3 activity. Such ligands include sequence-specific (or targeted) and sequence-nonspecific (or non-targeted) double stranded RNA having a length of 22 nucleotides or less. The double stranded RNA can be an siRNA, or any other double stranded RNA, as long as the length is 22 nucleotides or less. While the constructs containing the double-stranded RNA are effective when made with either blunt ends or with overhangs, if overhangs are used the nucleotides comprising the overhangs are considered part of 22 or less total nucleotides.

Thus, a double stranded RNA of 22 nucleotides or shorter the length includes those RNAs which contain some single stranded portion as long as a majority of the molecule has a double stranded RNA structure. Such double stranded RNAs include RNAs which have a double stranded central portion and having 3' overlaps of 1, 2, 3 or more nucleotides on the sense strand or antisense strand or both, such as overlaps of dT residues. The length of all single stranded and double stranded regions are added to determine the overall length of the double stranded RNA. For example, a double stranded RNA having a 16 nucleotide central double stranded RNA structure and 3' overlaps of dTdT on both the sense and antisense strands would have an overall length of 20 nucleotides. Double stranded RNAs are also contemplated which have one or more internal nucleotides which do not have a base pair. Double stranded RNAs also include those RNAs with no single stranded regions at all, such as a blunt end double stranded RNA of 22 nucleotides or less.

The siRNAs for use in the present invention are designed according to standard methods in the field of RNA interference. Introduction of siRNAs into cells may be by transfection with expression vectors, by transfection with synthetic dsRNA, or by any other appropriate method. Transfection with expression vectors is preferred. Alternatively, the cell exterior can be exposed to a composition containing the siRNAs of the present invention.

The expression vectors which can be used to deliver siRNA according to the invention include retroviral, adenoviral and lentiviral vectors. The expression vector includes a sequence which codes for a portion of a target gene or any other sequence whether specific for a particular gene or a nonsense sequence. The gene sequence is designed such that, upon transcription in the transfected host, the RNA sequence forms a hairpin structure due to the presence of self-complementary bases. Processing within the cell removes the loop resulting in formation of a siRNA duplex. The double stranded RNA sequence should be less than 23 nucleotides; preferably the dsRNA sequence is 15-22 nucleotides in length; more preferably the dsRNA sequence is 21 nucleotides in length, or 18 nucleotides in length, or 17 nucleotides in length, or 16 nucleotides in length, or 15 nucleotides in length.

The expression vectors may include one or more promoter regions to enhance synthesis of the target gene sequence. Promoters which can be used include CMV promoter, SV40 promoter, promoter of mouse U6 gene, and promoter of human H1 gene.

One or more selection markers may be included to facilitate transfection with the expression vector. The selection marker may be included within the expression vector, or may be introduced on a separate genetic element. For example, the bacterial hygromycin B phosphotransferase gene may be used as a selection marker, with cells being grown in the presence of hygromycin to select for those cells transfected with the aforementioned gene.

Cells can also be exposed to synthetic dsRNA of 22 nucleotides or less in length to provide antagonism of TLR3 activity. The synthetic dsRNAs are less than 23 nucleotides in length. Preferably the synthetic dsRNAs are 15-22 nucleotides in length. More preferably the dsRNAs are 20, 21 or 22 nucleotides in length, and may include 2-nucleotide 3' overhangs. In other embodiments, the synthetic dsRNAs may be 9, 15, 16, 17 or 18 nucleotides in length, and may include 2-nucleotide 3' overhangs. The 3' overhangs are preferably TT residues. Synthetic dsRNAs may be naked dsRNA, dsRNA containing one or more 2-O'-methyl groups, or dsRNA containing cholesterol conjugated to the 3' end of the sense or antisense strand. The double-stranded RNA may be conjugated to cholesterol, as the cholesterol assists the RNA in entering the cell. As shown in FIG. 16, the double stranded RNA requires a cell permeating entity to enter mammalian cells. Conjugation with cholesterol allows for effective internalization of the RNA.

Synthetic dsRNAs can be introduced into cells by injection, by complexing with agents such as cationic lipids, by use of a gene gun, or by any other appropriate method. Alternatively, the cell exterior can be exposed to a composition containing the synthetic dsRNAs of the present invention. The double-stranded RNA may be encapsulated in any pharmaceutically acceptable carrier, including, but not limited to, liposomes, nanoparticles, stable nucleic acid lipid particles (SNALPs), and dendrimers. Procedures involved in preparing these carriers are well known in the art, and so one skilled in the art could readily prepare the carriers for use with the present double-stranded RNA using conventional techniques.

The double-stranded RNA may be modified to help prevent degradation of RNAse, for example, using 2'O-Me or phosphori linkages.

Modulation of mammalian TLR3 function according to the present invention, through the antagonism of at least one functional characteristic of a mammalian TLR3, provides an effective and selective way of treating or preventing macular degeneration, such as inhibiting geographic atrophy. One or more antagonists of TLR3, such as those identified as described herein, can be used to treat or prevent macular degeneration, such as to inhibit geographic atrophy, for therapeutic purposes. The TLR3 antagonist may include, but is not limited to, a TLR3 antibody, a soluble TLR3, and a TLR3 small molecule antagonist.

Thus, the present invention provides a method of treating or preventing macular degeneration, such as inhibiting geographic atrophy, in an individual in need of such therapy, comprising administering a compound which antagonizes TLR3 function to an individual in need of such therapy. Such individuals include those having age-related macular degeneration, including dry macular degeneration.

In addition, the double-stranded DNAs described herein can be used to treat or prevent any disease or disorder in which administration of a TLR3 antagonist would be useful. Such diseases and disorders include diabetes, such as diabetes involving pancreatic beta cell apoptosis due to activation of the TLR3 and IRF-3 pathways; liver diseases such as those involving the immunoprivileged status of the liver controlled by TLR3 signaling; neurodegenerative diseases, such as those involving negative regulation of axonal growth by TLR3; viral and helminthic infections such as West Nile virus infection due to mediation of West Nile virus entry into the brain via TLR3, or respiratory syncytial virus (RSV) infection due to the involvement of TLR3 in RSV-induced chemokine expression, or infection by the helminth parasite Schistosoma due to its ability to use dsRNA to activate TLR3 in dendritic cells; and prevention of embryo resorption, i.e., spontaneous abortion, due to TLR3 modulation of pregnancy tolerance.

The methods of the present invention can be used in any mammalian species, including human, monkey, cow, sheep, pig, goat, horse, mouse, rat, dog, cat, rabbit, guinea pig, hamster and horse. Humans are preferred.

According to the method of the invention, one or more compounds can be administered to the host by an appropriate route, either alone or in combination with another drug. An effective amount of a compound is administered. An effective amount is an amount sufficient to achieve the desired therapeutic effect, under the conditions of administration, such as an amount sufficient for antagonism of TLR3 function, and thereby treating or preventing macular degeneration or other applicable disease or disorder.

A variety of routes of administration are possible including, but not necessarily limited to oral, dietary, topical, parenteral (e.g., intravenous, intraarterial, intramuscular, subcutaneous injection), inhalation (e.g., intrabronchial, intranasal or oral inhalation, intranasal drops), and intraocular injection routes of administration, depending on the disease or condition to be treated. Intraocular injection routes include periocular (subconjunctival/transscleral), intravitreous, subretinal and intracameral modes of injection.

Formulation of a compound to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Science, 16th Edition, Mack, Ed. 1980). For inhalation, the compound is solubilized and loaded into a suitable dispenser for administration (e.g., an atomizer, nebulizer or pressurized aerosol dispenser). As another example, a compound may be administered via a sustained release device or composition which is implanted in the vitreous humor, aqueous humor, on the sclera, in the sclera, in the suprachoroidal space, or in the subretinal space.

In another embodiment, the present invention provides a method for increasing the specificity of a desired siRNA target knockdown, i.e., a target gene which is not TLR3. The method comprises administering an amount of a target siRNA sufficient to knockdown a target gene and an amount of a double stranded RNA of 22 nucleotides or less which prevents the target siRNA from activating TLR3.

In another embodiment, the present invention provides methods for screening compounds that interact with TLR3. The present invention is useful for screening compounds by using TLR3 polypeptide or binding fragments thereof in any of a variety of drug screening techniques. The TLR3 polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between TLR3 and the agent being tested. Alternatively, one can examine the diminution in complex formation between TLR3 and its target cell, monocyte, etc. caused by the agent being tested.

Thus, the present invention provides methods of screening for drugs or any other agents which can affect macular degeneration or other applicable disease or disorder. These methods comprise contacting such an agent with a TLR3 polypeptide or fragment thereof and assaying (i) for the presence of a complex between the agent and the TLR3 polypeptide or fragment, or (ii) for the presence of a complex between the TLR3 polypeptide or fragment and the cell, by methods well known in the art. In such competitive binding assays, the TLR3 polypeptide or fragment is typically labeled. After suitable incubation, free TLR3 polypeptide or fragment is separated from that present in bound form, and the amount of free or uncomplexed label is a measure of the ability of the particular agent to bind to TLR3 or to interfere with the TLR3 and agent complex.

Another technique for drug screening provides high throughput screening for compounds having suitable binding affinity to the TLR3 polypeptide and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with TLR3 polypeptide and washed. Bound TLR3 polypeptide is then detected by methods well known in the art. Purified TLR3 can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding TLR3 specifically compete with a test compound for binding to TLR3 polypeptides or fragments thereof. In this manner, the antibodies can be used to detect the presence of any peptide which shares one or more antigenic determinants with TLR3.

The present invention also contemplates the use of drug screening assays in which drugs or any other agents are monitored in a bioassay, such as the ability of the drug or agent to inhibit geographic atrophy, such as inhibition of cell death in retinal pigmented epithelial cells. Such a drug screening assay may be used in conjunction with the various binding assays described above, i.e., drugs or other agents may be first tested for their ability to bind to TLR3, and those compounds having binding affinity for TLR3 are then tested in a bioassay, such as the ability of the drug or agent to inhibit geographic atrophy. Alternatively, the bioassay may be conducted with the drug or agent with or without a compound which stimulates the action of TLR3, such as a double-stranded RNA having a length greater than 22 nucleotides. Inhibition of geographic atrophy with the drug or agent but no or reduced inhibition of geographic atrophy with drug or agent in the presence of a compound which stimulates the action of TLR3 would be indicative of a drug or agent that inhibits geographic atrophy by interacting with TLR3. Similar screening assays can be performed comparing geographic atrophy in wild-type cells versus cells in which the genes for TLR3 are knocked out, with inhibition of geographic atrophy in wild-type cells due to exposure to drug or agent and no inhibition in the knockout cells being indicative of the drug or agent inhibiting geographic atrophy by interacting with TLR3.

The drug screening assays described above can be used not only to identify drugs useful for treating or preventing macular degeneration, but also for drugs useful for treating or preventing any other disease or disorder responsive to treatment with a TLR3 antagonist.

EXAMPLE 1

In Vitro Human RPE Cell Viability Assay

Primary human retinal pigmented epithelial (RPE) cells were isolated from eyes obtained from Advanced Bioscience Resources Inc. (Alameda, Calif.) after removing the vitreous humor and the neurosensory retina, then incubating in 2% Dispase (GIBCO, Madison, Wis.) in Hanks' balanced salt solution (HBSS) (Irvine Scientific, Santa Ana, Calif.) for 25 min at 37° C., and then passing through 70 μm and 40 μm nylon mesh filters (Falcon Plastics, Oxnard, Calif.). After centrifugation at 1500 rpm for 5 min, the fragments remaining in the filter were gently dissociated and seeded onto laminin-coated 6-well plates (Fisher Scientific, Tustin, Calif.). RPE cells were cultured in Dulbecco's Modified Eagle's Medium (DMEM, Irvine Scientific, Santa Ana, Calif.) with fetal bovine serum (FBS; 25% for primary culture and 10% thereafter) (Omega Scientific, Tarzana, Calif.), 100 μg/ml penicillin, 100 μg/ml streptomycin and 2 mM L-glutamine (Omega Scientific) at 37° C. in 95% air and 5% $CO_2$. At confluence, the cells were detached using 0.05% trypsin/0.02% EDTA (Irvine Scientific, Santa Ana, Calif.), collected by centrifugation and expanded. The purity of the RPE cell culture exceeded 95% as confirmed by immunohistological cytokeratin positivity and by the absence of contaminating $CD11b^+$ macrophages or $vWF^+$ endothelial cells. Cells were synchronized for cell cycle state by first cultivating them in high glucose DMEM (Gibco) supplemented with 10% FBS (Gibco) to achieve complete confluence and then by overnight serum starvation. They were passaged to 96-well plates at a density of 10,000 cells per well (60-70% confluence), followed by stimulation for 24 h with IFN-α/β (1000 U/mL, PBL Interferon Source) in high glucose DMEM with 2% FBS. Cultures were then treated with poly (I:C) (Invivogen) or poly (dI:dC) (Sigma-Aldrich) formulated in phosphate buffered saline. At 48 h, cell viability was measured with BrdU ELISA (Chemicon) according to manufacturer's instructions. Optical densities of 96-well plates were analyzed on a SpectraMax plate reader (Molecular Devices) at 450 nm using Softmax Pro v4.3. Differences in cell numbers were compared using Mann Whitney U test (SPSS 15.0 for Windows).

In Vitro Human RPE Apoptosis Assay

Cultures were sensitized with IFN-α/β for 24 h followed by treatment with either PBS or poly (I:C) (5 μg/mL) in high glucose DMEM (Gibco) with 2% FBS (Gibco). 24 h after treatment, cells were harvested with 0.05% trypsin-EDTA (Gibco), washed in PBS, and resuspended in annexin V staining buffer (BD Biosciences) at $10^6$ cells/mL. 100 µL aliquots were then incubated with 5 µL of FITC conjugated annexin-V (BD Biosciences) and 5 µL of propidium iodide (PI; BD Biosciences) for 15 min at 25° C. Cells were immediately analyzed and annexin $V^+/PI^-$ cells were calculated using Celiquest Pro (BD Biosciences).

In Vivo Mouse RPE Assays

Cell suspensions were isolated from RPE/choroid of C57BL6/J wild-type or Tlr3$^{-/-}$[22] mice (The Jackson Laboratory) 48 h after intravitreous injection of poly (I:C) (2 µg) by incubation with collagenase D (20 U/I; Roche Diagnostics). After treatment with Fc block (10 µg/ml; BD Biosciences) for 15 min on ice, $10^6$ cells were incubated with FITC-conjugated anti-mouse CD147 antibody (10 µg/ml, eBiosciences, Clone RL73) and APC-conjugated anti-mouse CD31 antibody (20 µg/ml; BD Biosciences, Clone MEC13.3) to identify CD147$^+$ CD31$^-$ RPE cells. For cell viability, cells were analyzed with a minimum of 10,000 gated events on a FACSCalibur flow cytometer (BD Biosciences), and CD147$^+$CD31$^-$ fractions were calculated with Cellquest Pro (BD Biosciences). For intracellular activated caspase-3 staining, CD147$^+$CD31$^-$ cells were subjected to fixation and permeabilization (Leucoperm, Serotec), followed by incubation with PE-conjugated rabbit anti-activated caspase-3 antibody (20 µl/$10^6$ cells, BD Biosciences, Clone C92-605) in the presence of 10% normal rabbit serum. Cells were analyzed with a minimum of 10,000 gated events on a FACSCalibur flow cytometer using Cellquest Pro. Differences in fractions of CD147$^+$ CD31$^-$ cells or activated caspase-3$^+$ cells were compared with the Mann Whitney U test.

CNV

Laser photocoagulation (532 nm, 200 mW, 100 ms, 75 µm) (OcuLight GL, IRIDEX Corporation) was performed on both eyes (4 spots per eye for volumetric analyses; 16 spots/eye for all other analyses) of each 6-8-week-old male mice to induce choroidal neovascularization (CNV) as previously described. CNV volumes were measured by a scanning laser confocal microscope (TCS SP, Leica) as previously reported with 0.5% FITC-conjugated *Griffonia simplicifolia* Isolectin B4 (Vector Laboratories) or 0.5% FITC-conjugated rat anti-mouse CD31 (BD Biosciences), or by cardiac perfusion with 5 mg/ml FITC-dextran (2 million average weight; Sigma-Aldrich). Pairwise correlations among volumes obtained by lectin, CD31, and dextran staining were highly correlated ($r^2>0.90$). CNV volumes per laser lesion were compared by hierarchical logistic regression using repeated measures analysis as previously described. Results are expressed as mean±s.e.m. Type-I error not exceeding 0.05 was deemed significant.

Drug Treatments siRNAs were formulated in siRNA buffer (20 mM KCl, 0.2 mM MgCl2 in HEPES buffer at pH 7.5; Dharmacon) or phosphate buffered saline (PBS; Sigma-Aldrich), as were poly I:C (Invivogen), poly dI:dC (Invivogen), or poly I:C$_{12}$U (Ampligen; Bioclones); and were injected into the vitreous cavity in a total volume of 1 µl with a 33-gauge Exmire microsyringe (Ito Corporation).

siRNA

All siRNAs were purchased from Dharmacon. Sense and anti-sense strands of siRNA were annealed per the manufacturer's instructions and formulated in either sterile siRNA buffer (Dharmacon, Inc.) or nuclease-free PBS.

| Sequences | |
|---|---|
| siRNA target | Sense Strand (5'→3') |
| Luc (23-nt) | UAAGGCUAUGAAGAGAUACdTdT (SEQ ID NO: 1) |
| Luc (22-nt) | UAAGGCUAUGAAGAGAUAdTdT (SEQ ID NO: 2) |
| Luc (21-nt) | UAAGGCUAUGAAGAGAUdTdT (SEQ ID NO: 3) |
| Luc (18-nt) | UAAGGCUAUGAAGAdTdT (SEQ ID NO: 4) |
| Luc (15-nt) | UAAGGCUAUGAdTdT (SEQ ID NO: 5) |
| Luc (9-nt) | UAAGGdTdT |

Chemical Modifications to siRNA-Luc

| | Sense strand | Anti-sense strand |
|---|---|---|
| Cholesterol | 3' conjugation | Unmodified |
| 2'O-methyl | Alternating substitutions, starting with first nucleoside | Alternating substitutions, starting with second nucleoside |

EXAMPLE 2

Mice were evaluated by dilated fundoscopic examination (1% tropicamide (Alcon). Retinal photographs were acquired on a TRC-50 IX camera (Topcon) with a digital imaging system (Sony).

Mice were dark adapted overnight and then anesthetized (Ketamine 50 mg/kg, Xylazine 10 mg/kg). Body temperature was maintained at 37° C. using a non-electric heating pad, and pupils were dilated using a 1% tropicamide. Both eyes were positioned within a ColorBurst Ganzfeld stimulator (Diagnosys). A reference electrode consisting of a platinum-needle was placed in the scalp equidistant from the ears, and the grounding electrode was placed subcutaneously in the flank. Silver wire loop electrodes constructed from commercially available micro-electrodes (Diagnosys) were placed on each of the corneal apices. Methylcellulose was then applied to ensure proper conductance. Espion software (Diagnosys) was used to program a fully automated flash intensity series from which retinal responses were recorded. The white flash intensity series was delivered in increasing increments of −5.0, −3.8, −2.6, −1.4, −0.2, 1.0 log cd·s/m². Interstimuli intervals were increased from 5 s at lowest to 90 s at highest. The numbers of averaging for each recording were 18 times at 1st step, and decreased to twice at final step. The a- and b-waves were designated as the minimal and maximal peak voltages, respectively. Data were analyzed using the Mann Whitney U test.

Frozen human retina sections were stored at −80 C. Prior to processing for IHC sections were dried at room temperature for 15 minutes, then fixed in 4% paraformaldehyde. Next the sections were rinsed in phosphate-buffered saline (PBS), pH 7.4, and blocked for 1 hour in 10% normal goat serum and 0.5% Triton X-100 diluted in PBS. Primary antibody to dsRNA (J2) was obtained from English & Scientific Consulting, Hungary. IgG2a was used as control. All antibodies were diluted in 1% normal goat serum and 0.05% Triton X-100 diluted in PBS. Primary and isotype control antibodies were incubated for overnight in cold room. Conventional immunohistochemistry was performed using a biotinylated goat anti-mouse secondary antibody (Vector Laboratories) followed by streptavidin-AP (Zymed). For colorimetric detection of the dsRNA we used the Alkaline Phosphate Substrate Kit III (Vector Blue). The substrate yields a blue reaction product. Slides were washed with deionized water, air-dried, and mounted in VectaMount (Vector Laboratories).

DSRNA sequences used included:

```
5-nt-dsRNA-chol: (Blunt)
Sense: CUAAG-3' Cholesterol
Antisense: CUUAG 7-nt-dsRNA-chol: (Blunt)
Sense: CUAAGGG-3' Cholesterol
Antisense: CCCUUAG 16-nt-dsRNA-chol: (with overhangs)
                                  (SEQ ID NO: 6)
Sense: UAAGGCUAUGAAGAdTdT-3' Cholesterol
                                  (SEQ ID NO: 7)
Antisense: UCUUCAUAGCCUUAdTdT
```

Figure 1:
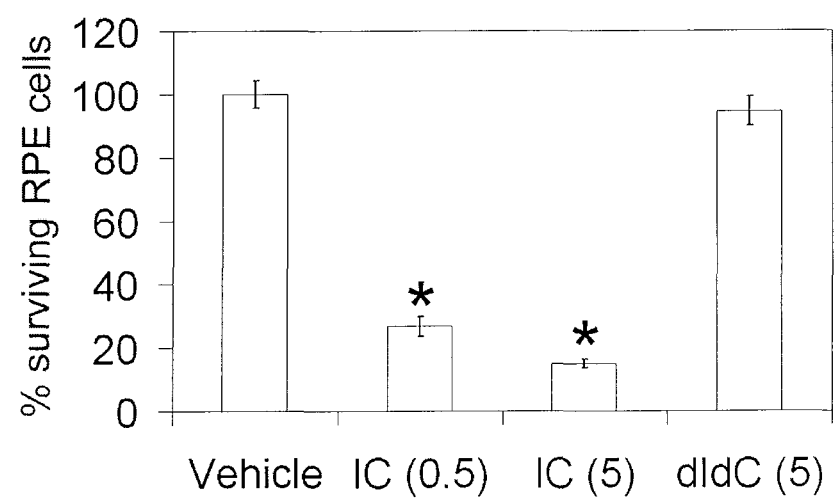
FIG. 1 illustrates the effect of poly (I:C) and poly (dI:dC) on survival of human retinal pigmented epithelial cells.
Figure 2:
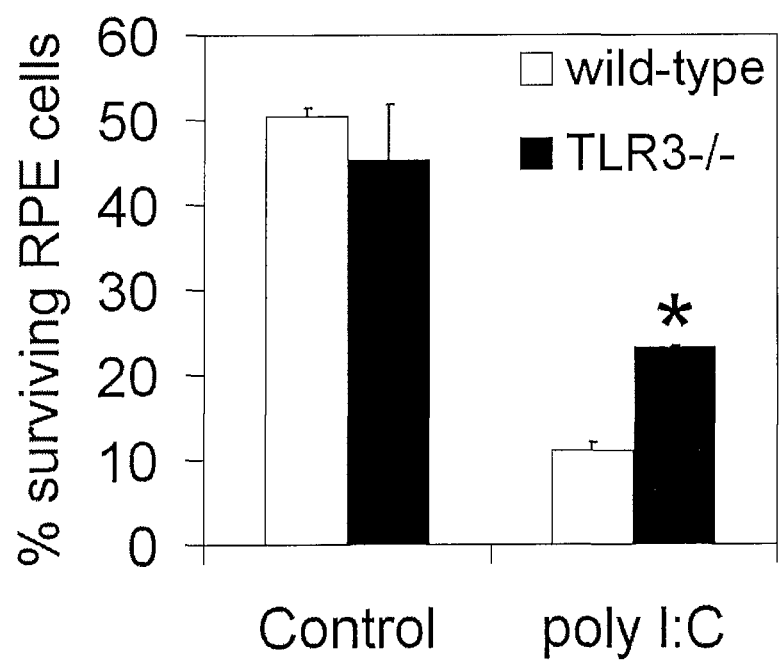
FIG. 2 shows the effect of intravitreous administration of poly (I:C) on survival of retinal pigmented epithelial cells from wild-type and Tlr3$^{-/-}$ mice.
Figure 3:
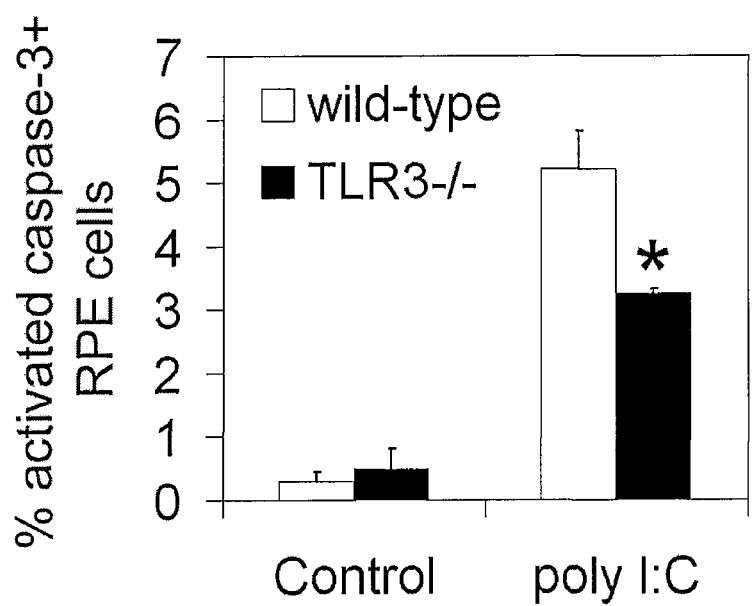
FIG. 3 illustrates the effect of intravitreous administration of poly (I:C) on activated caspase-3 expression in retinal pigmented epithelial cells from wild-type and Tlr3$^{+/+}$ mice.
Figure 4:
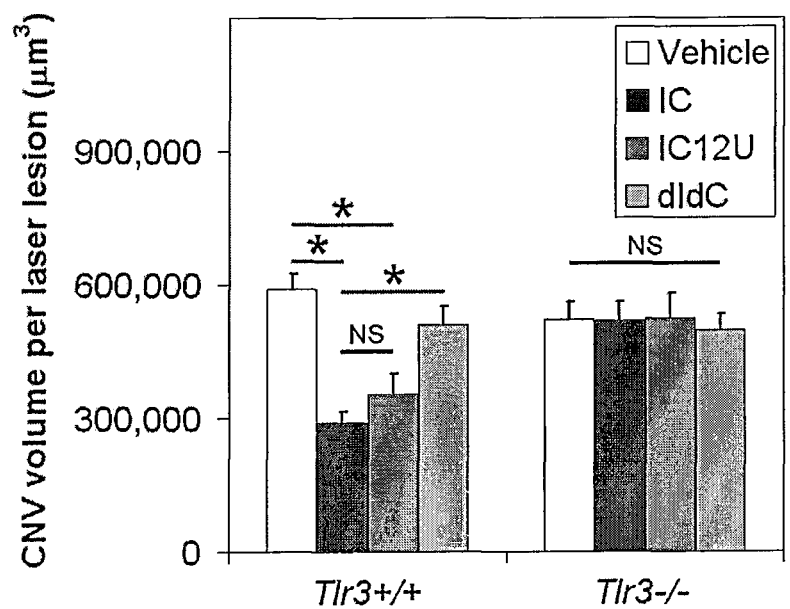
FIG. 4 shows the effect of intravitreous administration of poly (I:C), poly (I:C$_{12}$U) and poly (dI:dC) on choroidal neovascularization (CNV) in Tlr3$^{+/+}$ and Tlr3$^{-/-}$ mice.
Figure 5:
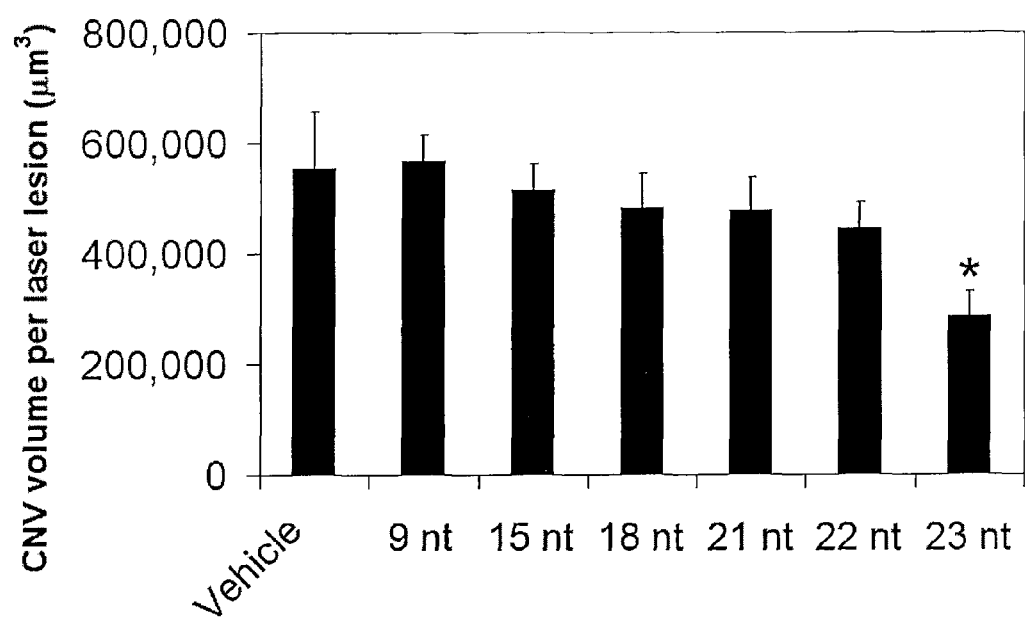
FIG. 5 illustrates the effect of 9 to 23 nucleotide versions of siRNA-Luc on CNV in wild-type mice.
Figure 6:
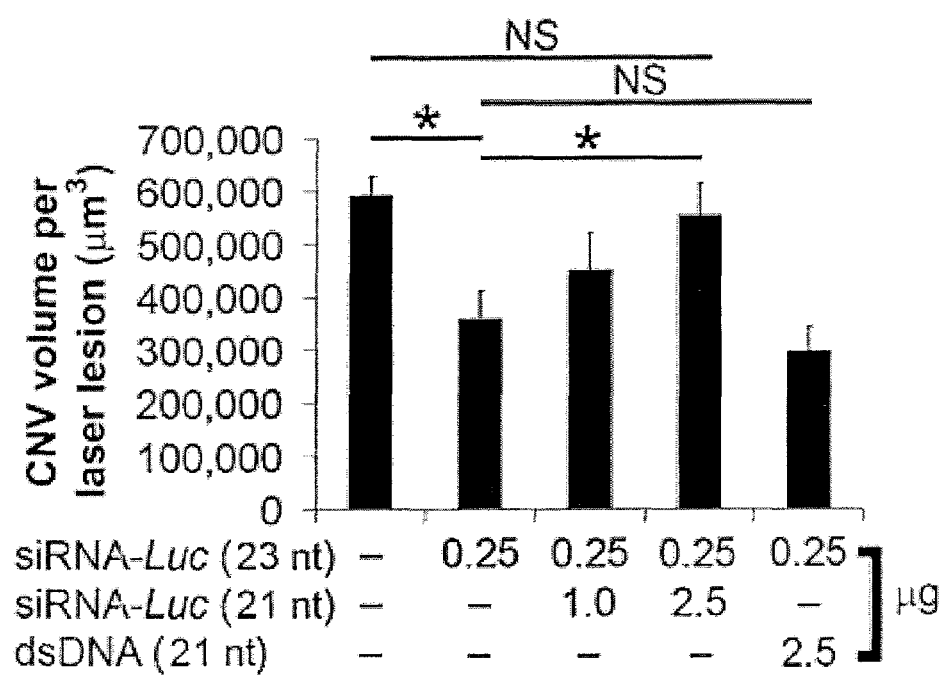
FIG. 6 shows the effect of 21-nt siRNA-Luc and 21-nt dsDNA on the ability of 23-nt siRNA-Luc to suppress CNV in wild-type mice.
Figure 7:
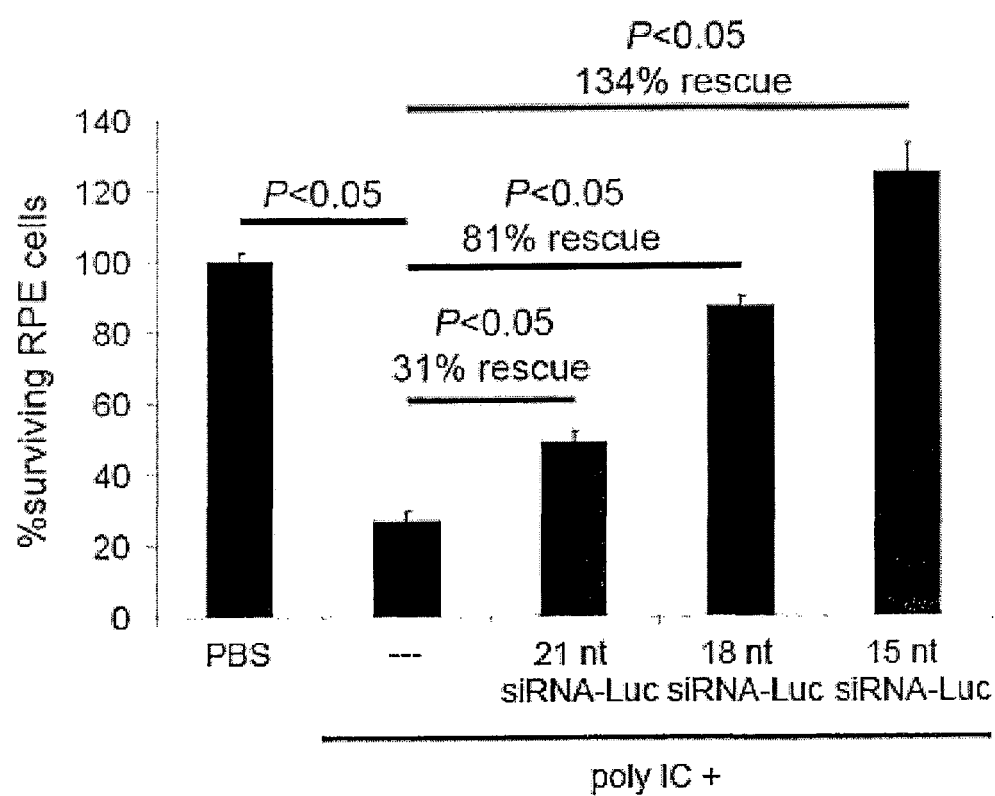
FIG. 7 illustrates ability of 2'O-methyl-21-nt siRNA-Luc-cholesterol, 2'O-methyl-18-nt siRNA-Luc-cholesterol, and 2'O-methyl-15-nt siRNA-Luc-cholesterol to rescue human retinal pigmented epithelial cells from poly (I:C) induced cytotoxicity.
Figure 8:
FIG. 8 shows immunohistochemistry using a monoclonal anti-long dsRNA Ab (J2), which reveals blue reaction product in drusen (arrow), RPE, Bruch's membrane and choriocapillaris (asterisk, collectively) in a donor eye of an 84-year-old patient with GA (a). Isotype control Ab revealed no specific immunostaining in another region of the same eye (b). J2 did not stain the retina or choroid of a 78-year-old patient without AMD (c). Images are representative of 5-7 eyes per group.
Figure 9:
FIG. 9 provides color fundus photographs showing that intravitreous administration of Ampligen® (poly I:C12U; 2 μg), a double stranded RNA that specifically activates TLR3, induces retinal degeneration (arrows) in wild-type C57Bl/6J mice (left panel) but not in TLR3−/− mice (right panel). The photographs were taken 10 days after Ampligen® injection.
Figure 10:
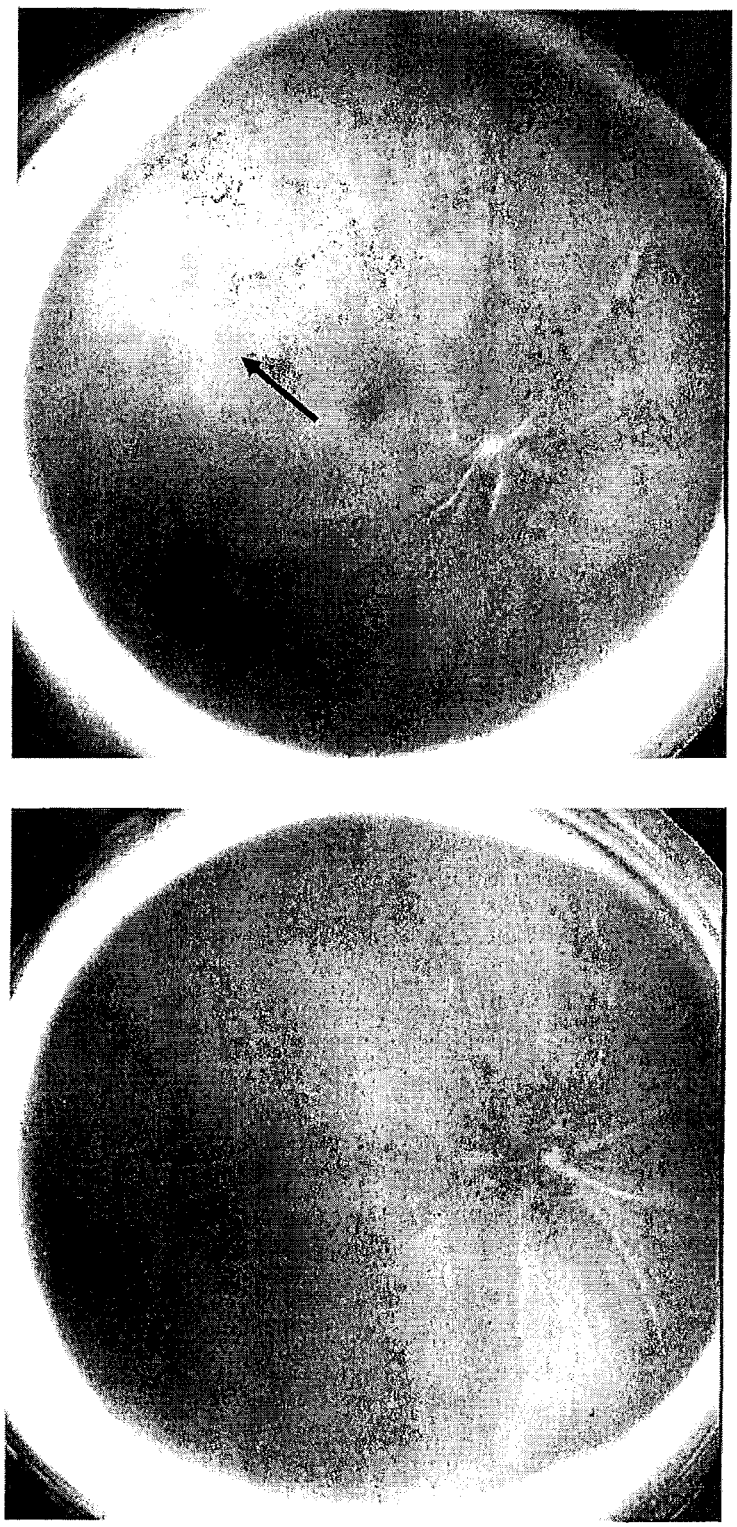
FIG. 10 provides color fundus photographs showing that intravitreous administration of Ampligen® (poly I:C12U; 2 μg) in wild-type mice does not cause retinal degeneration when neutralizing anti-TLR3 antibody (eBioscience; 12 μg) is co-administered (left panel). It was further shown that isotype control antibody (IgG; Jackson Immunoresearch; 12

As seen in FIG. 8, the TLR3 ligand poly (1:C) dose-dependently (0.5-5 μg/ml) reduced the survival of primary human retinal pigmented epithelial cells (hRPECs) compared to vehicle (phosphate buffered saline) or to poly (dI:dC), which does not activate TLR3. *P<0.01; n=4. The prototypic TLR3 ligand polyinosinic:polycytidylic acid (poly (I:C)), a synthetic long dsRNA that activates TLR3, induced cell death in primary human RPE cells in a dose-dependent fashion, consistent with the known cytotoxic effect of TLR3 activation. In contrast, polydeoxyinosinic:polydeoxycytidylic acid (poly (dI:dC)), which does not activate TLR3, did not reduce RPE cell viability. As seen in FIG. 8, intravitreous administration of poly (I:C) (2 μg) induced significantly less death of RPE cells (viability defined as fraction of $CD147^+CD31^-$ cells in the RPE/choroid layers) in $Tlr3^{-/-}$ mice than in wild-type mice (48.6±0.4% vs 78.1±2.0%; *P=0.03 by Mann Whitney U test; n=4). FIG. 10 shows the effect of intravitreous administration of poly (I:C) on activated caspase-3 expression in retinal pigmented epithelial cells from wild-type and $Tlr3^{-/-}$ mice. Intravitreous administration of poly (I:C) (2 μg) induced activated caspase-3 expression in a greater fraction of RPE cells in wild-type mice than in $Tlr3^{-/-}$ mice (5.2±0.6% vs 3.3±0.1%; *P=0.03; n=4). There was no significant difference in the fraction of activated caspase-3 expressing RPE cells between mice of different genotypes under control (baseline) conditions (P=0.76; The effect of TLR3 activation on RPE cells in vivo was studied by administering poly (I:C) into the vitreous humor of wild-type or $Tlr3^{-/-}$ mice. Poly (I:C) administration resulted in a 61±4% (P=0.03) greater loss of RPE cell numbers in wild-type mice compared to $Tlr3^{-/-}$ mice (FIG. 2). Similarly, there was a 60±18% (P=0.03) greater induction of RPE cell apoptosis (defined as caspase-3 activation) in wild-type mice compared to $Tlr3^{-/-}$ mice following poly (I:C) administration (FIG. 1). Collectively, these in vitro and in vivo data demonstrate a capacity for TLR3 activation to trigger cell death in RPE cells, which is considered the inciting event in the pathogenesis of geographic atrophy in age-related macular degeneration.

As seen in FIG. 11, intravitreous administration of 2 μg of polyinosinic:polycytidylic acid (I:C) and poly (I:$C_{12}$U) (Ampligen®, wherein uridine replaces cytosine statistically at every 13th nucleoside; I:$C_{12}$U), but not polydeoxyinosinic:polydeoxycytidylic acid (dI:dC; 2 μg), suppressed CNV in $Tlr3^{+/+}$ mice but not in $Tlr3^{-/-}$ mice. Vehicle (PBS); n=5-9, *P<0.05; NS, not significant. Poly (I:C) activates TLR3 as well as other dsRNA sensors such as MDA5. Poly (I:$C_{12}$U) activates only TLR3 and not other dsRNA sensors. Thus, the results demonstrate that poly (I:C) suppresses CNV via TLR3 since poly (I:C) and poly (I:$C_{12}$U) equally suppress CNV in $TLR3^{+/+}$ mice and do not suppress CNV in $TLR3^{-/-}$ mice.

As seen in FIG. 12, a 23-nt version of siRNA-Luc suppressed CNV in wild-type mice; however, shorter truncated versions did not do so. n=8-11, *P<0.05 compared to vehicle (buffer). Equimolar amounts comparable to 1 μg of 23-nt siRNA-Luc. These data demonstrate that siRNA duplexes shorter than 23-nt do not activate TLR3. FIG. 13 shows the effect of 21-nt siRNA-Luc and 21-nt dsDNA on the ability of 23-nt siRNA-Luc to suppress CNV in wild-type mice. 21-nt siRNA-Luc (1-2.5 μg), but not 21-nt dsDNA (2.5 μg), antagonized the ability of 23-nt siRNA-Luc (0.25 μg) to suppress CNV in wild-type mice. Reagents were injected intravitreously. n=7-11, *P<0.05, NS, not significant. Excess 21-nt siRNA-Luc prevented CNV suppression by 23-nt siRNA-Luc in a dose-dependent manner, suggesting that the shorter siRNA functioned as an inactive competitor of TLR3 monomers and interfered with the ability of the longer siRNA to bind and activate TLR3. The specificity of this competition was demonstrated by the inability of a dsDNA analogue of 21-nt siRNA-Luc to interfere with CNV suppression by 23-nt siRNA-Luc.

FIG. 16 illustrates the ability of 2'O-methyl-21-nt siRNA-Luc-cholesterol, 2'O-methyl-18-nt siRNA-Luc-cholesterol and 2'O-methyl-15-nt siRNA-Luc-cholesterol to rescue human retinal pigmented epithelial cells from poly (I:C) induced cytotoxicity. Poly (I:C) (1 μg/ml) induced cytotoxicity of primary human retinal pigmented epithelial cells (compared to PBS-phosphate buffered saline) was rescued by serum stable 2'O-methyl-21-nt siRNA-Luc-cholesterol (0.5 μg/ml)(31% rescue). Greater rescue of poly (I:C) induced cytotoxicity was induced by 2'O-methyl-18-nt siRNA-Luc-cholesterol (81% rescue), and even greater rescue by 2'O-methyl-15-nt siRNA-Luc-cholesterol (134% rescue). There was no cytotoxicity induced by 21-nt siRNA-Luc alone. n=4. These findings provide an example of how siRNA duplexes shorter than 23-nt can act as TLR3 antagonists.

All references cited in this disclosure are incorporated by reference to the same extent as if each reference had been incorporated by reference in its entirety individually.

While the invention has been described in detail and with reference to specific embodiments thereof, it will be apparent to one skilled in the art that various variations and modifications can be made therein without departing from the spirit and scope thereof. All such variations and modifications are intended to be included within the scope of this disclosure and the present invention and protected by the following claims.

I claim:

1. A method of treating or preventing macular degeneration comprising exposing a retinal or choroidal cell to a toll-like receptor 3 (TLR3)-antagonistic effective amount of a double-stranded RNA of 21 nucleotides or shorter length which binds to but does not activate the activity of a TLR3.

2. The method of claim 1, wherein macular degeneration is treated or prevented by inhibiting the geographic atrophy of wet or dry macular degeneration.

3. The method of claim 1, wherein the double-stranded RNA is a naked double-stranded RNA or a double-stranded RNA having an O-methyl group at one or more 2'-positions.

4. The method of claim 1, wherein the double-stranded RNA has 5-15 nucleotides.

5. The method of claim 4, wherein the double-stranded RNA has 7-11 nucleotides.

6. The method of claim 1, wherein the double-stranded RNA has 2-nucleotide 3' overhangs on the sense strand and the antisense strand.

7. The method of claim 1, wherein the double-stranded RNA is conjugated to cholesterol.

8. The method of claim 1, wherein the double-stranded RNA is encapsulated in a pharmaceutically acceptable carrier selected from the group consisting of liposomes, SNALPS, nanoparticles, and dendrimers.

9. The method of claim 1, wherein the double-stranded RNA is modified to prevent RNAse degradation.

10. The method of claim 9, wherein the double-stranded RNA is modified with 2'O-Me.

11. The method of claim 1, wherein the double-stranded RNA is a sequence-nonspecific double-stranded RNA.

12. The method of claim 1, wherein the double-stranded RNA is a sequence-specific double-stranded RNA.

13. The method of claim 1, wherein the retinal cell is a retinal pigmented epithelial cell.

14. The method of claim 1, wherein the choroidal cell is a choroidal endothelial cell.

15. The method of claim 1, wherein the double-stranded RNA is administered via a sustained release device or composition which is implanted in the vitreous humor, aqueous humor, on the sclera, in the sclera, in the suprachoroidal space, or in the subretinal space.

16. A method of treating or preventing a disease or disorder associated with activation of TLR3 comprising exposing a subject in need thereof to a toll-like receptor 3 (TLR3)-antagonistic effective amount of a double-stranded RNA of 21 nucleotides or shorter length which binds to but does not activate the activity of a TLR3.

17. The method of claim 16, wherein the disease or disorder is selected from the group consisting of diabetes, a liver disease, a neurodegenerative disease, a viral infection, a helminthic infection, and prevention of spontaneous abortion.

18. A method for increasing the specificity of a desired siRNA target knockdown, the method comprising administering an amount of a target siRNA sufficient to knockdown a target gene and an amount of a double stranded RNA of 21 nucleotides or less which prevents the target siRNA from activating TLR3.

* * * * *